US00PP10532P

United States Patent [19]

Kuiken

[11] Patent Number: Plant 10,532

[45] Date of Patent: Aug. 4, 1998

[54] HYBRID TEA ROSE PLANT NAMED 'RUIKUIROS'

[75] Inventor: Kwekerij Jan Kuiken, En Tzummarum, Netherlands

[73] Assignee: De Ruiter's Nieuwe Rozen B.V., Pl De Kwakel, Netherlands

[21] Appl. No.: 759,606

[22] Filed: Dec. 5, 1996

[51] Int. Cl.[6] ..... A01H 5/00

[52] U.S. Cl. ..... Plt./18

[58] Field of Search ..... Plt./18, 17, 19

[56] References Cited

U.S. PATENT DOCUMENTS

P.P. 8,528 1/1994 de Ruiter ..... Plt./18

*Primary Examiner*—Howard J. Locker
*Attorney, Agent, or Firm*—Christie, Parker & Hale, LLP

[57] ABSTRACT

A new variety of hybrid tea rose plant producing salmon pink flowers of good form and suitable for growing under glass.

1 Drawing Sheet

BACKGROUND OF THE PRESENT INVENTION

The present invention relates to a new and distant variety of rose plant of the hybrid tea rose class which was discovered as a naturally occurring mutation in a controlled planting of the variety 'Ruirovingt', U.S. Plant Pat. No. 8528. The varietal denomination of the new variety is 'Ruikuiros'. The new variety was isolated and asexually reproduced by budding in Holland.

SUMMARY OF THE INVENTION

Among the novel characteristics possessed by this new variety which distinguish it from its parent and all other varieties of which I am aware are its attractive salmon pink flowers of good form borne on a floriferous plant with long stems and suitable for production of cut flowers under glass. The new variety can be reproduced through propagation by cuttings, grafting, budding and micropropagation.

Asexual reproduction by budding of the new variety as performed in Holland shows that the foregoing and other distinguishing characteristics come true to form and are established and transmitted through succeeding propagations.

Comparison With Parent

'Ruikuiros' is a mutation of 'Ruirovingt' (U.S. Plant Pat. No. 8,528), with a different flower color. The color of 'Ruirovingt' is a mix of pink, yellow, cream and the color of 'Ruikuiros' is salmon pink.

BRIEF DESCRIPTION OF ILLUSTRATION

The accompanying illustration shows typical specimens of the vegetative growth and flowers of the new variety in different stages of development depicted in color as nearly true as it is reasonably possible to make the same in a color illustration of this character.

DESCRIPTION OF THE NEW VARIETY

The following is a detailed description of the new variety, with color terminology in accordance with The Royal Horticultural Society Colour Chart (RHSCC) and horticultural terminology in accordance with standard terminology used in UPOV-approved horticultural guideline. The terminology used in color descriptions herein refers to plate numbers in the aforementioned color chart. Phenotypic expression may vary depending upon growing conditions under different climate, soil, and cultivation conditions.

Parentage: Mutation of 'Ruirovingt'.
Class: Hybrid Tea.

As can be seen in the accompanying detail illustration there is shown a new shoot, 1; compound three, five and seven leaflet leaves, 2, 3 and 4, respectively; a stem, 5; buds, 6 and 7; a flower, 8, about one-third open; and a flower, 9, more fully open. Also shown are flower stems 10, 11 and 12, with reproductive organs displayed.

The following further horticultural description is based on observations made of specimens grown under glass in Holland.

Flower

Blooming habit: Nearly continuous.

A. Bud:

(1) *Size.*—Medium, about 3 to 4 cm long and about 2 to 3 cm wide.

(2) *Form.*—Ovate (shape of longitudinal section just before separation of sepals); urn-shaped after sepals part.

(3) *Color.*—As sepals divide, near 55B to 55C with near 5A near base on upper side and near 4C on underside.

(4) *Sepals.*—Slightly longer than green bud, generally simple to slightly foliated, near 138A; lower surface coloration of sepals is near 144A, upper surface coloration of sepals is near 148C.

(5) *Peduncle.*—Long: Strength-erect, very strong. Color-medium green, near 147B to 147C, few hairs or prickles, about 9 cm long.

B. Bloom:

*Flower.*—Medium; viewed from above — irregularly rounded; viewed from side —(a) upper part of fully opened flower, flattened convex; (b) lower part of fully opened flower, flattened convex.

(1) *Size.*—Average size when fully expanded — about 7 to about 8 cm.

(2) *Borne.*—Singly, one to a stem, stem length about 50 cm.

(3) *Form.*—Pointed center, exhibition type, somewhat flat top, spiral imbricated, outer petals roll under.

(4) *Petalage.*—About 25, about 14 petaloids, about 3×3 cm.

(5) *Color.*—After sepals part and petals unfurl top surface appears near 36A to 36D; petal top surface (⅓ to full open) near 36B to 36C. As petals age color becomes grey/white and light pink, near 65D. Overall tonality from a distance is attractive salmon pink.

(6) *Peduncle.*—Generally smooth.

(7) *Fragrance.*—Slight to none.

(8) *Production.*—About 240 flower stems/$m^2$/year.

Petals:

(1) *Texture.*—Crisp.

(2) *Appearance.*—Inside velvety and outside satiny.

(3) *Form and size.*—Broad, medium, strong undulation of margin.

(4) *Arrangement.*—Regularly arranged, imbricated.

(5) *Petaloids.*—Several, about 14.

(6) *Lasting quality.*—Long-lasting quality on plant and after cutting, vaselife is about 15 to 20 days. Blooms on plant can be more than 30 days. After the flowers fades, the color becomes greenish.

Reproductive Organs

A. Stamens, filaments and anthers:

*Arrangement and color.*—Regularly arranged around styles; color of filaments — yellow.

B. Pollen:

*Color.*—Deep yellow, near 13A.

C. Styles: Long, stigma above mouth of receptacle, yellow.

D. Stigmas: Yellow, positioned below anthers.

E. Hip: Pitcher-shaped; large seed vessel at petal fall but few hips set seed. When seed is set hip is about 1.5 cm and color is green-orange.

Plant

A. Form: Narrow, bushy, average disease resistance.

B. Growth: Vigorous, about 1 m in height and about 0.5 m in width.

C. Foliage: Compound 3, 5 and 7 leaflets.

(1) *Size.*—Foliage size is about 15–20 cm. Foliage length of top is about 7 cm. Foliage width of top is about 5.5–6 cm. Veins are visible and often purple.

(2) *Quantity.*—Abundant.

(3) *Color.*—Juvenile foliage — red purple to bronze-reddish brown; near 180A; weak to medium anthocyanin coloration, (shoot about 20 cm long); mature leaf color—near 139A, undersurface near 138A.

(4) *Shape.*—Broad oval.

(5) *Texture.*—Upper side is medium glossy; underside is matte.

(6) *Edge.*—Serrate.

(7) *Serration.*—Ordinary, acuminate apices.

(8) *Leaf stem.*—Color — medium green, near 147A to 147B.

(9) *Stipules.*—Short, simple, medium green, distinct auricle.

(10) *Leaflets.*—Cross section — slight concave: strong undulation of margin; terminal leaflet — blade, broad, about 4 to 6 cm long and 4 to 5 cm wide, rounded base.

D. Wood:

(1) *New wood.*—Color—Near 172B, young shoots have weak to medium anthocyanin; coloration — bronze red purple to reddish brown.

(2) *Old wood.*—Color — medium green, near 147A to 147B.

E. Prickles (thorns):

(1) *Prickles.*—Present; quantity (main stalk) — few; shape of lower side — concave; Length — short prickles, absent or very few, long prickles very few to few; Color — near 159A; Position — irregular.

F. Disease resistance: Susceptible to powdery and downey mildew.

What is claimed is:

1. A new and distinct variety of rose plant of the hybrid tea rose class, substantially as shown and described.

* * * * *

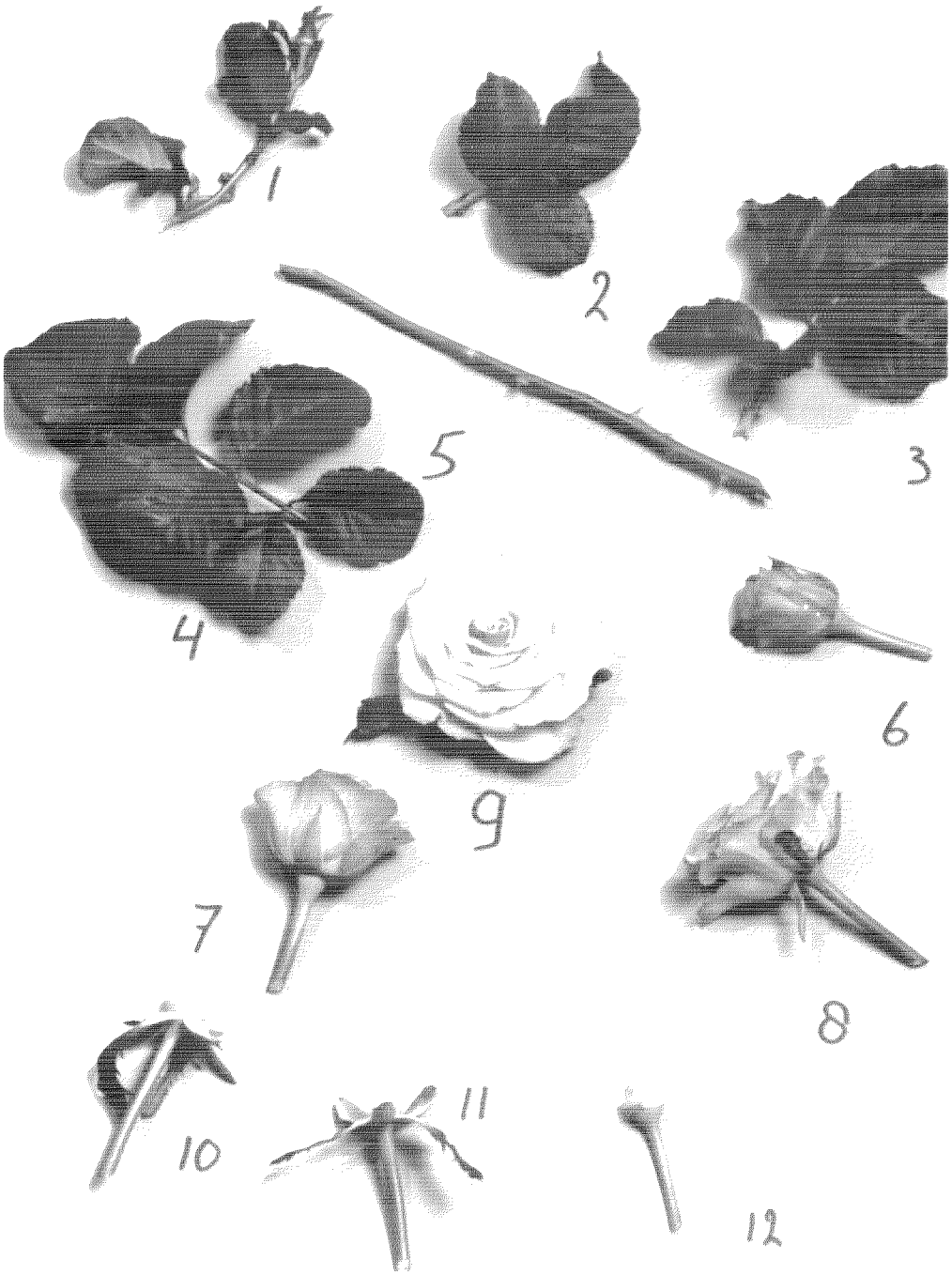
1
2
3
4
5
6
7
8
9
10
11
12